(12) United States Patent
Chen et al.

(10) Patent No.: US 8,758,009 B2
(45) Date of Patent: Jun. 24, 2014

(54) RESTORATIVE DENTAL APPLIANCES (75) Inventors: Yan Chen, Cupertino, CA (US);
Chunhua Li, Cupertino, CA (US)

(73) Assignee: Align Technology, Inc., San Jose, CA (US)

(*) Notice: Subject to any disclaimer, the term of this patent is extended or adjusted under 35 U.S.C. 154(b) by 717 days.

(21) Appl. No.: 12/055,010

(22) Filed: Mar. 25, 2008

(65) Prior Publication Data
US 2009/0246724 A1 Oct. 1, 2009

(51) Int. Cl.
*A61C 3/00* (2006.01)

(52) U.S. Cl.
USPC ...................... 433/6; 433/8; 433/24

(58) Field of Classification Search
USPC ........................... 433/6, 24, 215, 18
See application file for complete search history.

(56) References Cited

U.S. PATENT DOCUMENTS

| 4,526,540 | A  | * | 7/1985  | Dellinger ......................... 433/24 |
| 6,183,248 | B1 | * | 2/2001  | Chishti et al. .................... 433/6  |
| 6,390,812 | B1 | * | 5/2002  | Chishti et al. .................... 433/6  |
| 6,485,298 | B2 | * | 11/2002 | Chishti et al. .................... 433/6  |
| 6,705,861 | B2 | * | 3/2004  | Chishti et al. .................... 433/6  |
| 7,121,825 | B2 | * | 10/2006 | Chishti et al. .................... 433/6  |
| 2002/0142258 | A1 |   | 10/2002 | Chishti et al. |
| 2006/0078841 | A1 | * | 4/2006  | DeSimone et al. ............... 433/6 |
| 2006/0099544 | A1 |   | 5/2006  | Lai et al. |

FOREIGN PATENT DOCUMENTS

WO  WO-03003935  1/2003

OTHER PUBLICATIONS

ISA/EPO, International Search Report for International Application No. PCT/IB2009/000575, 3 pages, Sep. 25, 2009.

* cited by examiner

*Primary Examiner* — Hao D Mai (57) ABSTRACT

A dental appliance including a concave trough conforming to a plurality of teeth when placed over the plurality of teeth. The concave trough is configured to transition from a first shape to a second shape if a deforming force is applied. The concave trough further includes a shape memory material. The shape memory material is configured to restore the concave trough to an approximate first shape upon an application of an external stimulus. The first shape is configured to apply a first force on a tooth when the trough conforms.

17 Claims, 11 Drawing Sheets

RESTORATIVE DENTAL APPLIANCES

FIELD

Embodiments of the present invention relate in general to the field of orthodontics.

BACKGROUND

An alternative to braces includes the use of aligner-type dental appliances for realigning teeth. Such an appliance may be comprised of a thin concave trough of material that forms a receiving cavity geometry that generally conforms to a patient's teeth but is slightly out of alignment with the initial tooth configuration. Placement of the dental appliances over the teeth applies controlled forces in specific locations to gradually move the teeth into a new predetermined configuration. Repetition of this process with successive appliances comprising new configurations eventually moves the teeth through a series of predetermined intermediate arrangements along the most effective and efficient treatment path to a final predetermined arrangement.

Some dental appliances are made using polymers, such as thermoplastic polyurethane. Polymers may deform over time and/or use due to external and internal forces. Some deforming external forces may include repeated insertion/removal and biting/wearing. An internal deforming force may include material stress relaxation. The deformation may reduce tooth moving forces, thereby reducing the usefulness of the dental appliance. Once the usefulness of the aligner dental appliance is reduced, the dental appliance is typically disposed of, and either a replacement dental appliance is made or the next dental appliance in the treatment series is used. Hence, the shorter the effective usefulness of the dental appliance, the more frequently the dental appliance needs to be changed. Consequently, an extension of the effective usefulness of the dental appliance is desirable.

SUMMARY

A dental appliance is described herein. In one embodiment, the dental appliance comprises a concave trough conforming to a plurality of teeth when placed over the plurality of teeth. The concave trough is configured to transition from a first shape to a second shape if a deforming force is applied. The concave trough comprises a shape memory material. The shape memory material is configured to restore the concave trough to an approximate first shape upon an application of an external stimulus. The first shape is configured to apply a first force on a tooth when the concave trough conforms.

DESCRIPTION OF EMBODIMENTS

In the following description, numerous specific details are set forth in order to provide a thorough understanding. However, it will be recognized by one of ordinary skill in the art that embodiments may be practiced without these specific details. In other instances, well known methods, procedures, and components have not been described in detail as not to unnecessarily obscure aspects of the present invention.

Overview

Embodiments in accordance with the present invention transition the dental appliance from a deformed and/or relaxed shape to an original shape upon an application of an external stimulus thereby extending the useful lifespan of the dental appliance.

The dental appliance comprises a concave trough conforming to a plurality of teeth when placed over the plurality of teeth. In other words, upon placement, controlled forces are applied to the teeth as the appliance conforms in specific locations to gradually move the teeth into a new predetermined configuration. The concave trough comprises a shape memory material being transitionable to the approximate original shape from the relaxed shape upon an application of an external stimulus. The original shape is configured to apply a desired force on a tooth when the trough conforms. The deformed shape may have less than desirable forces acting on a tooth and may obtain this shape due to deforming forces, such as biting the dental appliance.

System and Method for Positioning Teeth

Figure 1:
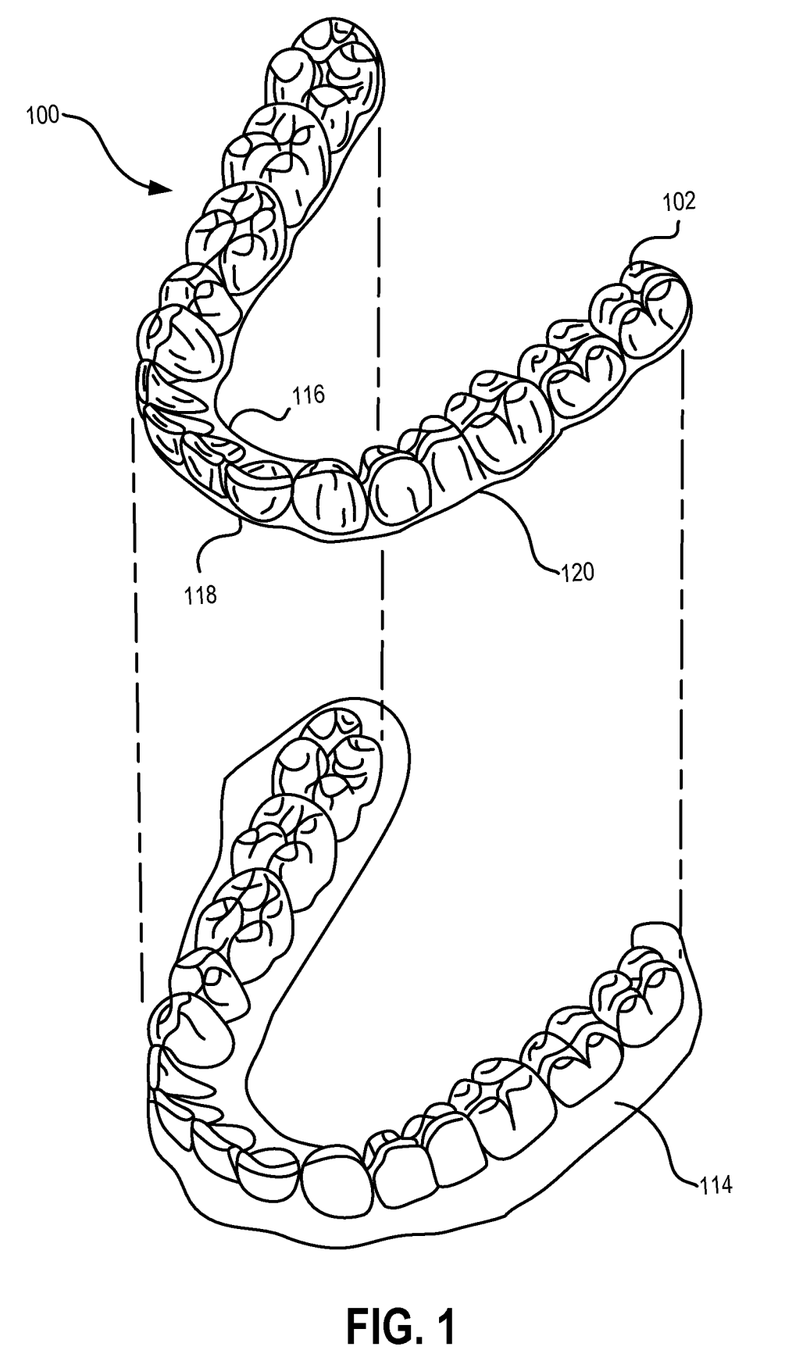
FIG. 1 illustrates the lower jaw of a patient together with a dental appliance upon which embodiments of the present invention may be implemented.

Referring to FIG. 1, the lower jaw 114 of a patient together with a dental appliance 100 is illustrated upon which embodiments of the present invention may be implemented. The dental appliance 100 is removable and replaceable over the teeth. In some embodiments, appliance 100 is one of a plurality of incremental position adjustment appliances.

The dental appliance 100 may comprise a polymeric concave trough 102 having an inner cavity 120, a proximal edge 116, and a distal edge 118. The inner cavity is shaped to receive and resiliently reposition teeth from one tooth arrangement to a successive tooth arrangement. In some embodiments, the polymeric concave trough 102 fits over all teeth present in the upper jaw (not depicted) or lower jaw 114. Typically, only certain one(s) of the teeth will be repositioned while others of the teeth will provide a base or anchor region for holding the dental appliance in place as it applies the resilient repositioning force against the tooth or teeth to be repositioned. Certain areas of the appliance will confer orthodontic forces on the teeth due to the intentional mismatch built into the appliance between the tooth's current position and the desired position built into the appliance. These are the inherently "active" regions of the appliance. Certain areas of the appliance will conform to the teeth nearly exactly as they are, without introducing orthodontic forces onto the teeth to which they conform. These are the inherently "passive" areas of the appliance which retain the teeth as they are in their current state.

The planning and fabrication of such dental appliances as an example elastic polymeric positioning appliance is described in detail in U.S. Pat. No. 5,975,893, and in published PCT application WO 98/58596 which designates the United States and which is assigned to the assignee of the present application, and which is herein incorporated by reference for all purposes. Systems of dental appliances employing technology described in U.S. Pat. No. 5,975,893, are commercially available from Align Technology, Inc., Santa Clara, Calif., under the tradename, Invisalign System. Align Technology, Inc., is the assignee of the present application.

Throughout the body of the Description of Embodiments, the use of the terms "aligner" or "dental aligner" is synonymous with the use of the terms "appliance" and "dental appliance" in terms of dental applications. For purposes of clarity, embodiments are hereinafter described within the context of the use and application of appliances, and more specifically "dental appliances."

Securing Dental Appliance to Teeth

Figure 2:
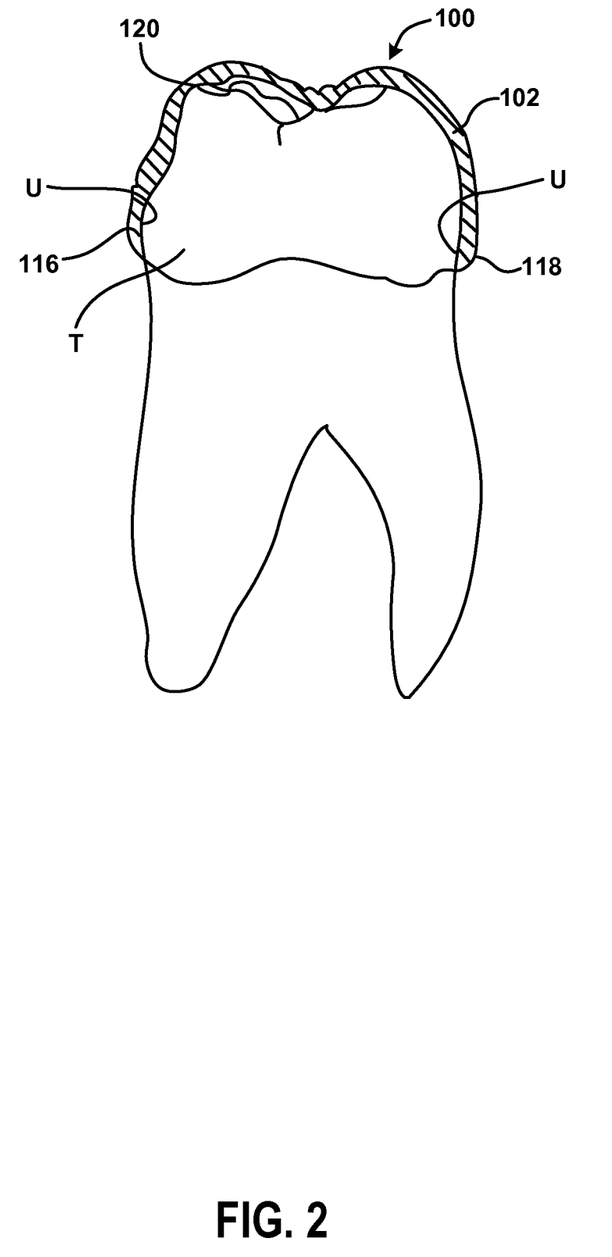
FIGS. 2, 2A, and 2B are cross-sectional views of an embodiment for securing the appliance of FIG. 1 on to the teeth, in accordance with embodiments.
Figure 2A:
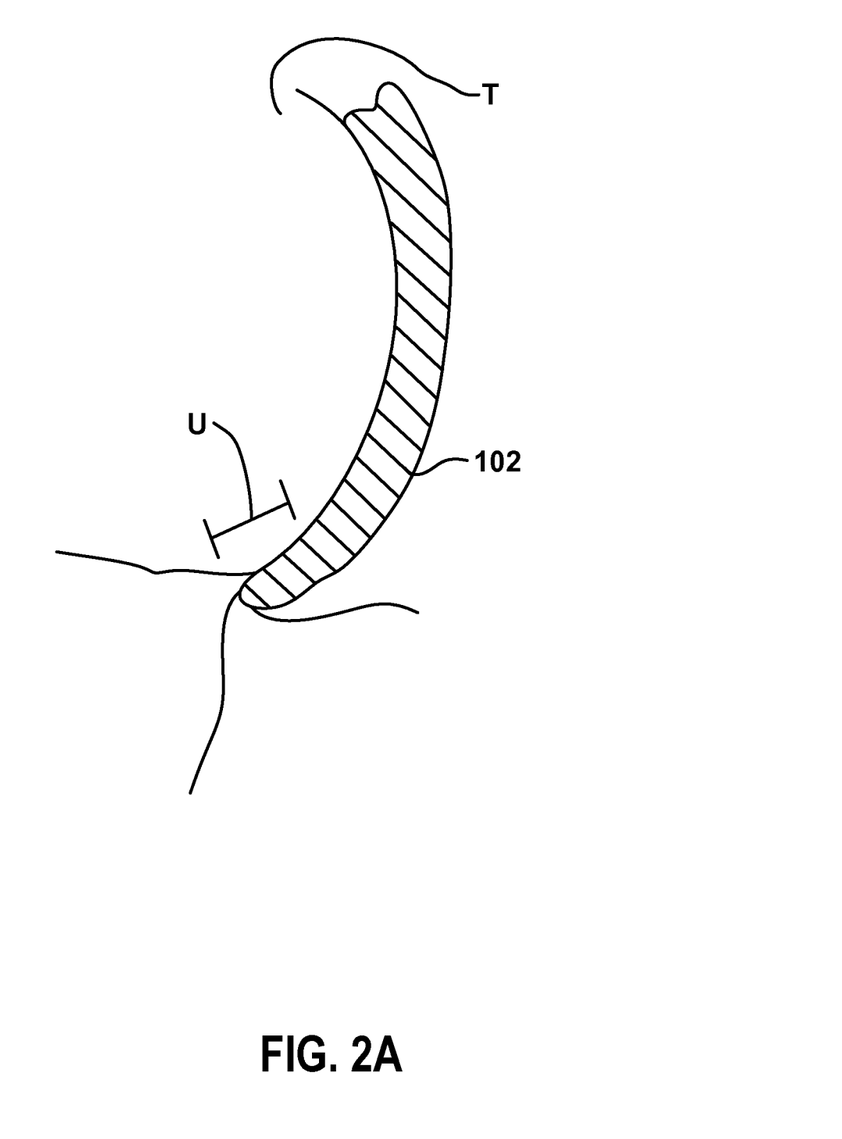
Figure 2B:
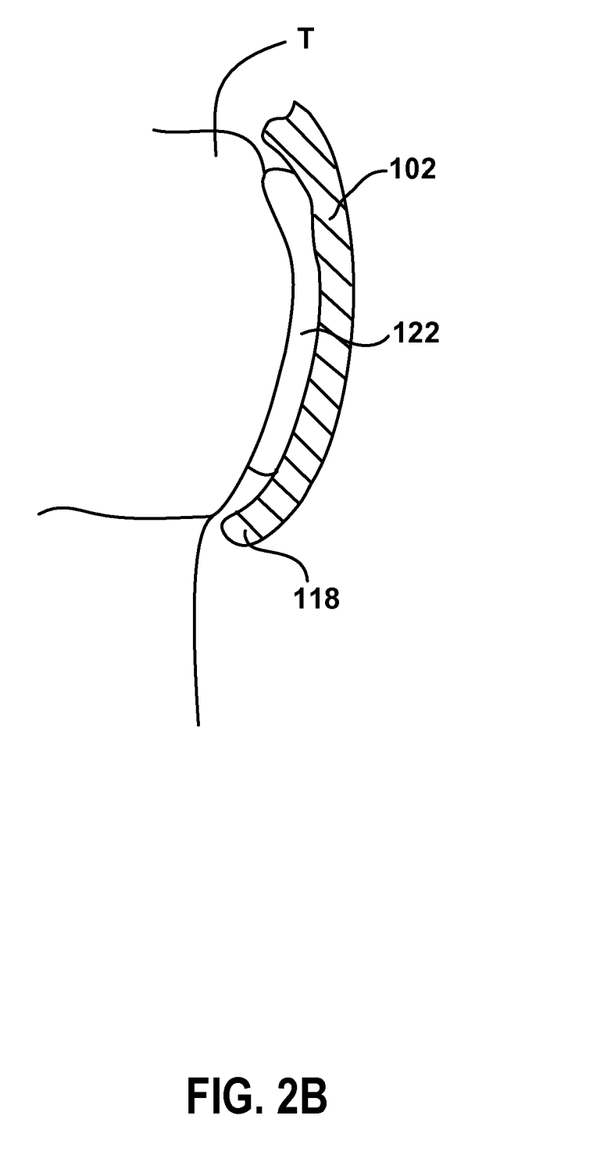

As may be understood with reference to the cross-sectional views of embodiment for securing the appliance of FIG. 1, in FIGS. 2, 2A, and 2B, the concave trough 102 is forced down over teeth T, typically by the patient biting down on the concave trough or by other forms of manual pressure being applied to the concave trough. Edges 116 and 118 are made to engage what is known as the undercut U of the teeth. Typically, this type of engagement is helpful in that it allows for specific tooth movements, such as extrusions (e.g., upward movement of the tooth).

The concave trough 102 is made of a material that has a predetermined modulus, also referred to as the stiffness, of the material. Generally, the modulus is a measurement of the inherent stiffness of a material determined by conducting stress and strain tests on a material specimen and plotting the results. The value of the slope of the line generated by the results is the modulus. The modulus can be predetermined to match the compliance required to reposition the teeth based on requirements set by an individual patient's repositioning needs. In one example, the concave trough may have a modulus in the range of between about 0.1 GPa to 4 GPa, usually 0.5 GPa to 3 GPa, and preferably about 0.8 GPa to 1.5 GPa.

In various embodiments, the concave trough 102 is formed from a material that has uniform properties, such as stiffness, over the entire area. In some embodiments, the concave trough has varying stiffness, thickness, or other material properties at different points or segments. In other embodiments, other layers, reinforcement elements, holes, or components may be added to the concave trough 102 to vary the stiffness and/or other mechanical properties. The stiffness of the concave trough 102 may keep edges 116 and 118 engaged with undercut U, which is configured to hold the appliance in place and effect tooth repositioning.

The concave trough 102 may include a single or a plurality of polymeric material layers. In some embodiments, each layer may have shape memory materials, as discussed further herein. The layers may consist of similar and/or different materials. The shape memory materials may undergo a property change independent of one another or simultaneously. The layer or layers may also be made of a cross-linked polymer capable of undergoing a joint change in shape.

Figure 3:
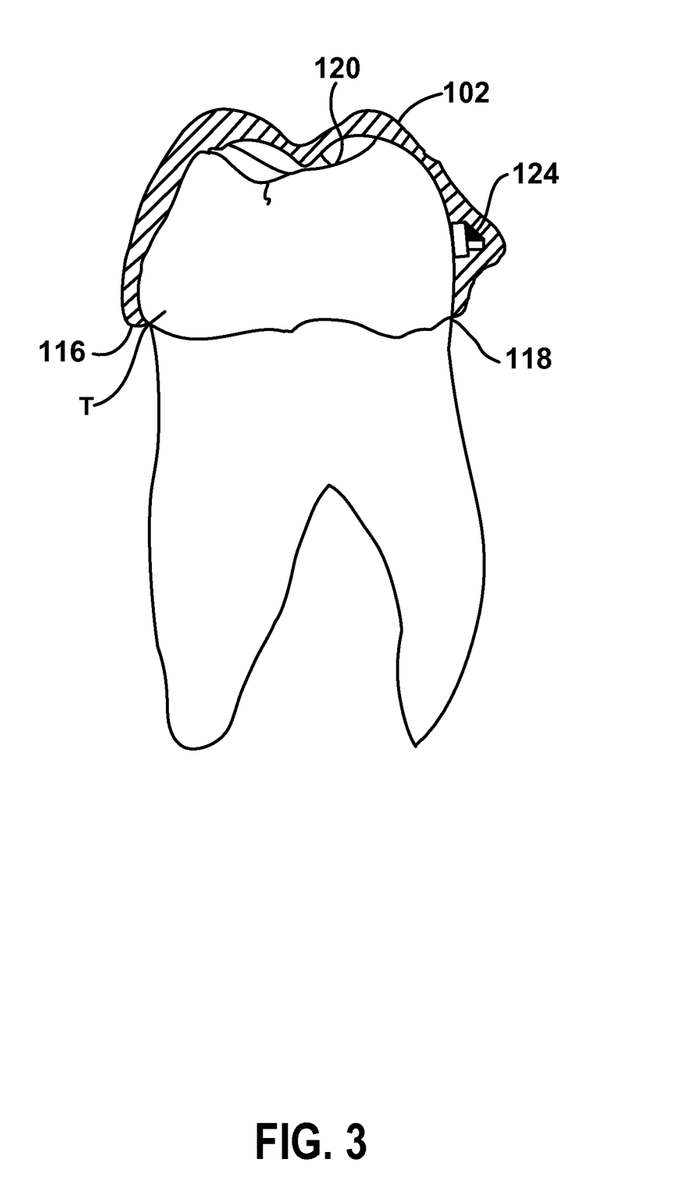
FIG. 3 illustrates a cross-sectional view of an attachment device for securing the appliance of FIG. 1 on to the teeth, in accordance with embodiments.

FIG. 3 illustrates a cross-sectional view of an attachment device for securing the appliance of FIG. 1 on to the teeth, in accordance with embodiments. In another alternative embodiment, concave trough 102 may also be held or anchored to the teeth through an engagement between concave trough 102 and an attachment device 124, such as an anchor. The attachment device 124 may be anchored to a distal surface (between tooth and cheek) and/or a proximal surface (between tooth and tongue) of the teeth using an adhesive or similar bonding substance. In various embodiments, the anchors may have any of a variety of material properties with the objective being to point a force-transmitting interface between the appliance and the tooth when the appliance is in place. The anchors may be formed from most solid, physiologically acceptable materials, particularly metals, ceramics, and polymers. The materials may be rigid, resilient, and/or programmable, e.g. shape memory polymers or metal alloys. In some instances, it is also possible that the anchors would be mechanically complex, e.g. articulated, rotatable, or otherwise repositionable to facilitate mounting or removal of the appliance from the teeth.

Several techniques for securing the dental appliance to the teeth, such as, anchoring, use of adhesive, and gripping are described in U.S. Pat. No. 6,390,812 B1, which is herein incorporated by reference for all purposes.

Deforming Forces

Although the dental appliance 100 may be designed to resist deformation, some regions of the dental appliance 100 may experience deformation. Deformation may reduce the forces to reposition the teeth. Deformation may be caused by inserting the dental appliance, removing the dental appliance, wearing the dental appliance, biting the dental appliance, material stress relaxation, heating, cooling, or any force that stresses the dental appliance.

Dental Appliance Material Properties

In various embodiments, the dental appliance uses shape memory material to restore the dental appliance to the approximate original shape upon the application of an external stimulus or stimuli. Some shape memory materials that may be used include shape memory polymers, methacrylate containing polymers, acrylate containing polymers, elastomer polymers, thermoplastic polymers, thermoplastic elastomer polymers, thermoset polymers, thermoplastic polymer blends, cross-linked thermoplastic polymers, and cross-linked thermoplastic polymer blends.

The dental appliance 100, in some embodiments, has a polymeric material layer fabricated into at least two segments, one segment harder than the other segment. In other embodiments, a softer segment is fabricated using a polymeric material and the harder segment is made using polymeric material and/or non-polymeric material. The softer segment may be designed more susceptible to deform under deforming forces than the harder segment. The harder segment may be designed to control a restoration of an original shape. Upon an application of an external stimulus, the softer segment controlled by the harder segment's forces returns the dental appliance 100 to the approximate original shape.

The external stimulus may be a non-oral application. A non-oral application is any application outside of a mouth as the application may be damaging to the mouth and/or surrounding region.

The dental appliance 100 may be configured with a reinforcement structure, such as a wire, a filament, a mesh, a ring, and/or a braid. The reinforcement structure may also be capable of undergoing a change in material property and/or a change in shape, such that the change facilitates the restoration of the original shape. For example, dental appliance 100 may be fabricated with a polymeric outer layer and a metal inner wire embedded in at least a portion of the appliance proximate to either the engagement with the undercut or the engagement with the anchor. The metal inner wire may be made of a shape memory metal, such as Nitinol.RTM., Bimetal.RTM., Memotal.RTM. or similar alloy. The wire undergoes a change in material property (and/or shape) as it is subjected to a thermal stimulus or other external stimulus. In this example, the wire changes geometry. Since the wire is embedded within the dental appliance, the appliance also changes shape, which may restore the appliance to an approximate original shape.

The changes described above may be provided through use of various polymers which undergo a glass transition at a preselected temperature. The glass transition may occur by using a plastic, such as a polymer, that has a molecular transition incorporated in the same. The polymeric material is biocompatible and is formulated so that the achieved transition can be activated upon subjecting the appliance to thermal stimuli as herein explained. The molecular transitions, which are incorporated in the appliance, are typically in the form of thermotransitions, as for example, a crystalline melting point, above about 37 degrees Celsius, preferably between 40 degrees Celsius and 55 degrees Celsius, of the polymer side chain, the polymer main chain, or a liquid-crystal (mesophase) transition of the polymer chain. The thermotransitions may also be accessed via a glass transition phenomenon or a local mode molecular transition.

Dental Appliance Layers

Figure 4A:
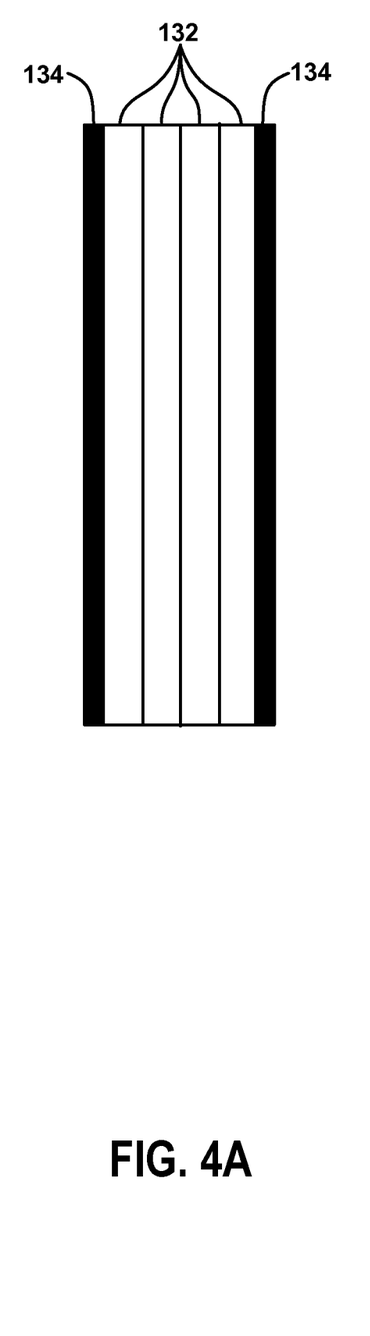
FIGS. 4A-4D illustrates layering geometry, in accordance with embodiments.
Figure 4B:
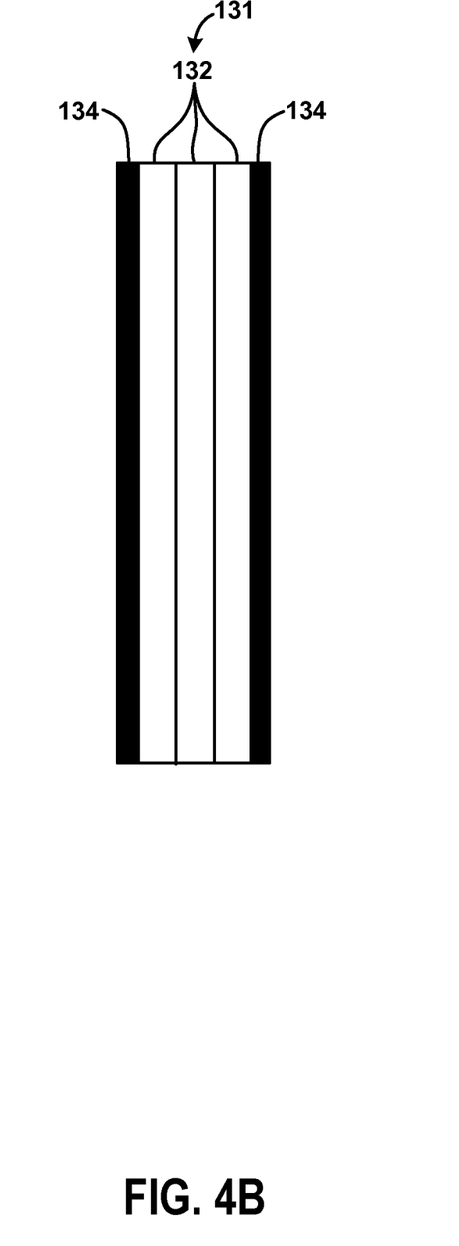
Figure 4C:
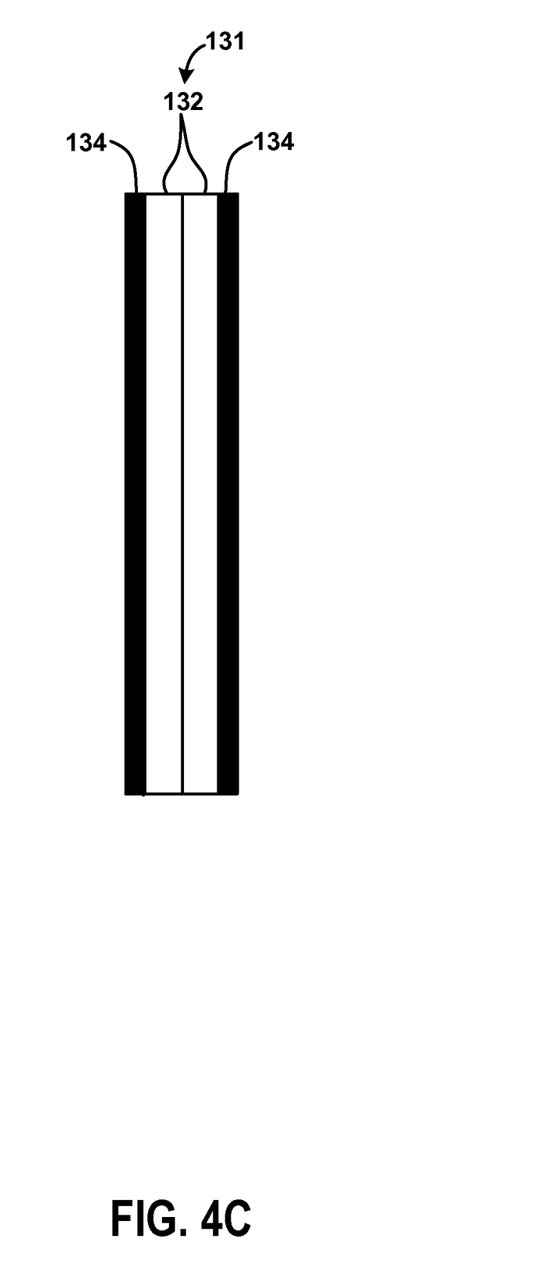
Figure 4D:
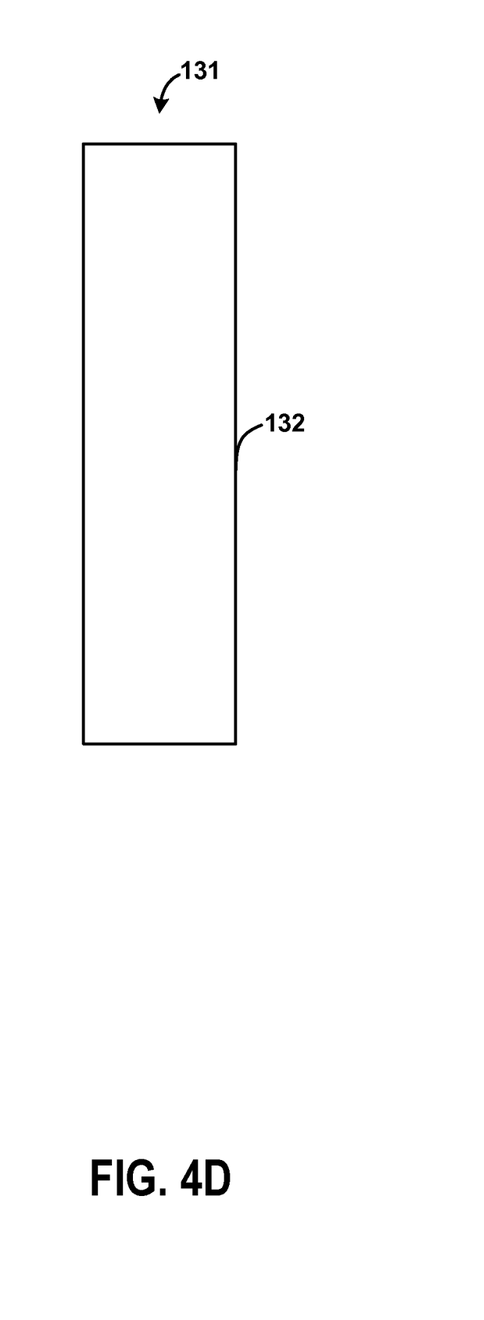

FIGS. 4A-4D illustrates layering geometry, in accordance with embodiments. In various embodiments, an original shape restoration mechanism may comprise the concave trough 102 with a single layer as shown in FIG. 4D or a plurality of layers, as shown in FIGS. 4A, 4B and 4C. In various embodiments, the layer 132 of FIG. 4D includes a single material with a thickness ranging from about 1 mil to 60 mils, and preferably 10-40 mils.

The concave trough 102 may include a variable number of inner layers 132. For example, four, three or two inner layers 132, as shown in FIGS. 4A, 4B, and 4C, respectively. More than four inner layers (not depicted) may also be used. The inner layers 132, as well as the outer layers 134, may each have different thickness, such as 5 or 10 mils, and/or variable glass transition temperatures. The layers may be formed in various orientations and configurations to suit the modulus and application requirements. The layers may be formed by a process, such as thermoforming or similar process, such as co-extrusion, lamination, or any other process where layers are formed. The layers may be formed with cavities and indentations used as repositioning forces on the teeth.

An example embodiment is to have Polycarbonate outer layers 134 and the PVC inner layers 132. Here, while under a glass transition temperature of both materials, the forces of all layers have a combined modulus that may be used as forces to grab hold of and reposition the teeth. If desired to restore the dental appliance to an original shape, heat may be applied to obtain the glass transition temperature of the inner layers. The forces of the inner layers will relax, transition, and may eventually return to a previous alignment, thereby allowing the dental appliance to return to an approximate original shape. Alternatively, the inner layers may be configured with a higher transition temperature than that of the outer layers. By reversing the threshold glass transition temperatures between the layers, the rolls of the inner and outer layers may be reversed.

In various embodiments, the softer segment may consist of one or more layers and the harder segment may consist of one or more layers. In still further embodiments, the softer segment may consist of multiple layers with different glass transition temperatures, thereby allowing different levels of restoration depending on different degrees of deformation.

Several examples using glass transition materials and layers are described in U.S. Pat. No. 6,390,812 B1, which is herein incorporated by reference for all purposes.

Cross-Sectional View of the Dental Appliance

Figure 5:
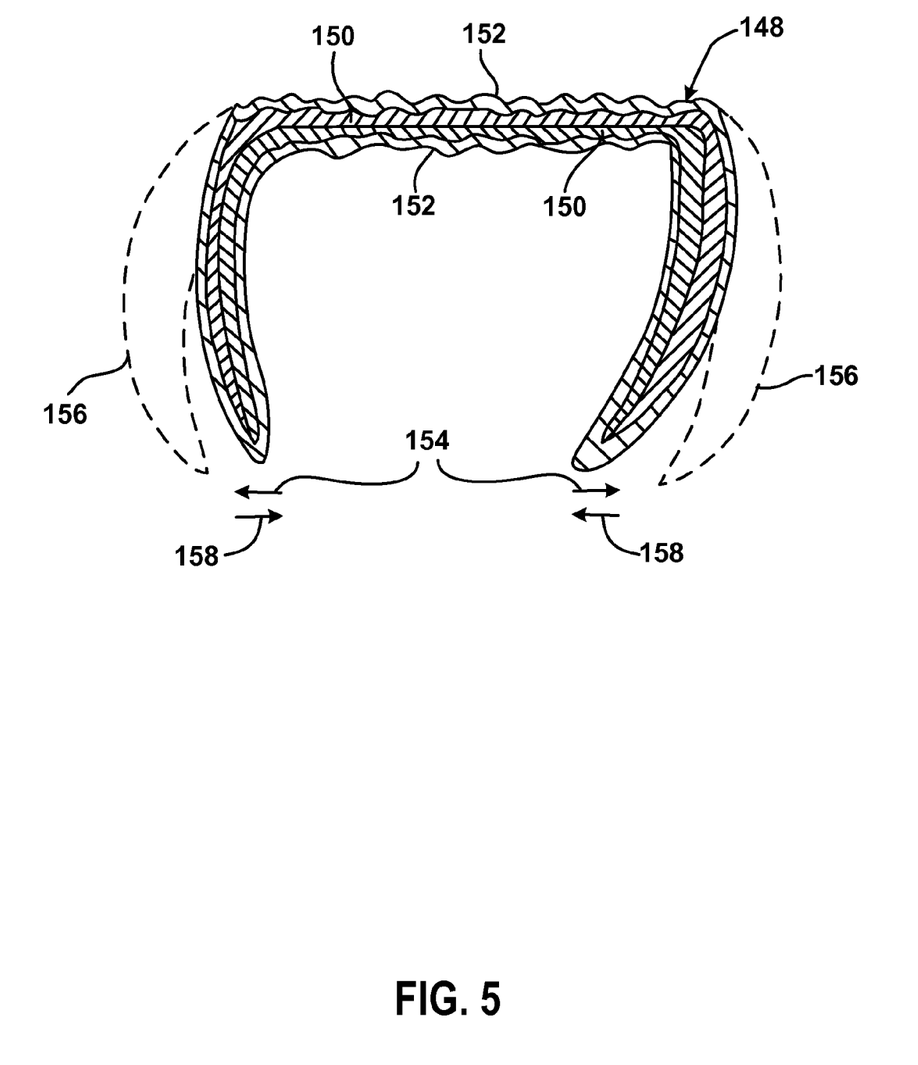
FIG. 5 illustrates a cross-sectional view of a dental appliance transforming shapes, in accordance with embodiments.

FIG. 5 illustrates cross-sectional view of a dental appliance 148 transforming shapes, in accordance with embodiments. The cross section view of the dental appliance 148 shows several layers, such as inner layers 150 and an outer layer 152. The dental appliance is shown in an original shape. Deforming forces 154, as discussed herein, may deform the dental appliance 148 to a shape as shown by dotted lines 156.

In various embodiments, a plurality of inner layers 150 is sandwiched between the outer layer 152. The inner and outer layers may have variable thickness and variable glass transition temperatures depending on the modulus requirements. The inner layers 150 and outer layer 152 may be made from a homopolymer, cross-linked homopolymer, copolymer, polycarbonate, cross-linked copolymer, a copolymer blend of thermoplastics, and/or similar material. The outer layer 152 may have a higher (or lower) glass transition temperature than the inner layers 150. The inner and outer layers are formed with the desired surface features and indentations necessary for proper application of the repositioning forces to the teeth. The layer or layers with the lower glass transition temperature may be the softer segment, as discussed herein. The layer or layers with the higher glass transition temperature may be the harder segment, as discussed herein.

During an application of an external stimulus, the softer segment heats to a temperature higher than or equal to the glass transition temperature of the softer segment. The temperature of the harder segment is maintained at a temperature below the glass transition temperature of the harder segment. This is desirable as the harder segment may be used to control the shape of the dental appliance 148. As the softer segment reaches the glass transition temperature, the material softens, repositions, and remolds to the shape of the harder segment. The harder segment via returning forces 158 restores the dental appliance 148 to the approximate original shape. As the dental appliance 148 cools below the glass transition temperature of the softer segment, the softer segment hardens and increases the stiffness of the dental appliance 148.

Although the glass transition temperature is described as the threshold temperature for activating the state change process of the appliance, alternatively, the melting point temperature may be used as the threshold temperature. An advantage to using the melting point temperature is a greater change in properties from one state to another. Also, the change in properties occurs over a smaller temperature range.

External Stimulus

Depending on the shape memory material, some external stimuli may include heat, chemicals, light, magnetic forces, cleaning, and a pH agent. The external stimulus may be used to initiate the state changes in various embodiments described herein. For example, the heat may be supplied to the appliance by introducing a source of heat energy, such as a liquid with high heat transfer capacity. High heat transfer capacity may allow for uniform heating of the dental appliance, thereby more effectively returning the appliance to the original shape. In various embodiments, two or more external stimuli may be used, for example, using a cleaning device for cleaning that applies a magnetic force and/or heat and/or uses chemicals and hydraulic forces.

Similarly magnetism, electricity, and radio waves can be used as secondary sources of heat to cause the desired state changes. Such external heat can also be applied by using an infrared, microwave, or radio frequency sources as well as resistive heating. Use of pH agents on pH sensitive materials and other stimuli having an effect on shape memory materials are described in U.S. Pat. No. 6,390,812 B1, which is herein incorporated by reference for all purposes.

Restoring the Dental Appliance's Original Shape

Figure 6:
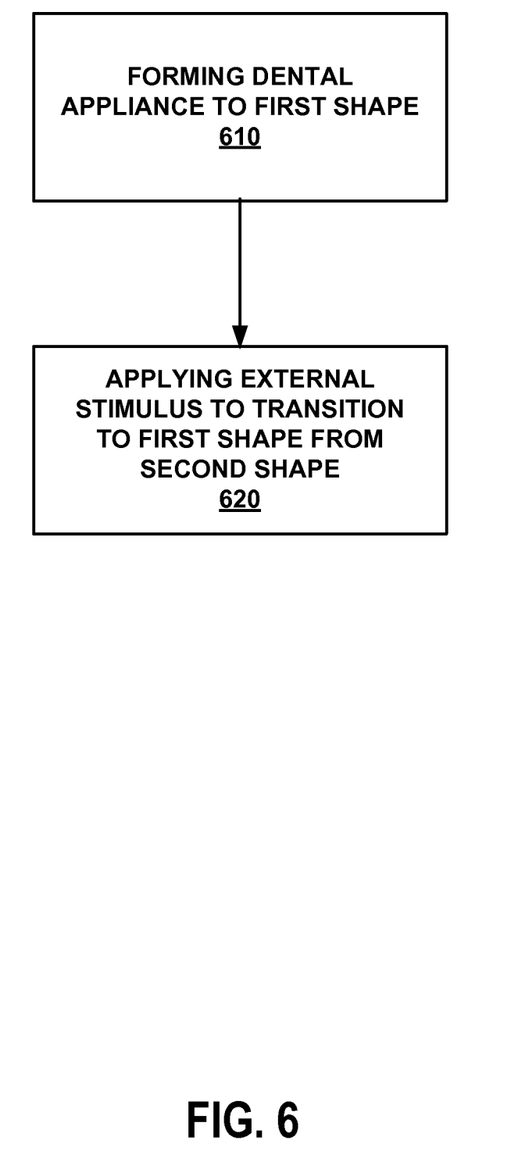
FIG. 6 is a flow chart of a method for restoring a dental appliance, in accordance with embodiments.

FIG. 6 is a flow chart of a method for restoring a dental appliance, in accordance with embodiments. In step 610, the dental appliance is formed to an original shape. The dental appliance may consist of one or a plurality of polymeric layers and/or non-polymer materials. Deforming forces may deform the dental appliance.

In step 620, an external stimulus is applied to the dental appliance to transition to the approximate original shape from the deformed shape. In various embodiments, the external stimulus heats the softer segment to a temperature greater than the glass transition of the softer segment. As the softer segment is heated, the deformed forces deforming the softer segment are relaxed, thereby allowing the harder segment to mold the softer segment and restore the dental appliance to an approximate original shape. In various embodiments, the approximate original shape is within zero to five mils of the original shape. In other embodiments, the approximate original shape is effectively the original shape regarding desirable teeth aligning forces. After the dental appliance cools below the glass transition temperature of the softer segment, the softer segment aligns and strengthens the stiffness of the dental appliance.

While the embodiments illustrated in steps 610-620 show specific sequences and quantity of steps, the present invention is suitable to alternative embodiments. For example, not all the steps provided for in the methods are required for the present invention. Furthermore, additional steps may be added to the steps presented in the present embodiment. Likewise, the sequences of steps can be modified depending upon the application.

Various alternatives, modifications, and equivalents may also be used. For example, a non-polymeric material, such as a metal, may be used for the softer and/or harder segment. Therefore, the above description should not be taken as limiting the scope of the invention which is defined by the appended claims.

Embodiments of the present invention, a restorative dental appliance, have been described herein. While the invention is described in conjunction with various embodiments, it is understood that they are not intended to limit the invention to these embodiments. On the contrary, the invention is intended to cover alternatives, modifications and equivalents, which may be included within the spirit and scope of the invention as defined by the appended claims.

What is claimed is:

1. A dental appliance comprising:
   a concave trough configured to transition from a first shape to a second shape when a deforming force is applied to the dental appliance, wherein the first shape conforms to a plurality of teeth when placed over the plurality of teeth and applies a first force on the plurality of teeth, wherein the concave trough comprises:
   a shape memory material configured to restore the concave trough from the second shape to an approximate first shape upon an application of an external stimulus, the approximate first shape configured to apply the first force on the plurality of teeth, wherein the shape memory material comprises:
   a first segment being an inner layer, wherein the first segment comprises:
   a first glass transition temperature; and
   a second segment coupled with the first segment, the second segment being an outer layer and enclosing the inner layer, wherein the second segment comprises:
   a second glass transition temperature, wherein the first glass transition temperature is less than the second glass transition temperature,
   wherein upon the application of the external stimulus which comprises heat to cause a temperature to be reached that is higher than or equal to the first glass transition temperature and below the second glass transition temperature, the second segment, being harder than the first segment, controls the first segment via forces to return the concave trough to the approximate first shape, such that as the first segment reaches the first glass transition temperature, the first segment undergoes a state change, molding to a shape of the second segment while the forces of the second segment return the concave trough to the approximate first shape.

2. The dental appliance of claim 1, wherein the shape memory material comprises a material selected from the group consisting of shape memory polymers, methacrylate containing polymers, acrylate containing polymers, elastomer polymers, thermoplastic polymers, thermoplastic elastomer polymers, thermoset polymers, thermoplastic polymer blends, cross-linked thermoplastic polymers, cross-linked thermoplastic polymer blends, metal alloys, and shape memory metals.

3. The dental appliance of claim 1, wherein the concave trough comprises a plurality of polymeric layers.

4. The dental appliance of claim 1, wherein the second shape is configured to apply a second force on the tooth, the first force being greater than the second force.

5. The dental appliance of claim 1, wherein the deforming force comprises a force from the group consisting of inserting, removing, wearing, biting, heating, cooling the dental appliance, and material stress relaxation of the dental appliance.

6. The dental appliance of claim 1, wherein the external stimulus is a non-oral application.

7. The dental appliance of claim 1, wherein the external stimulus is induced using a cleaning device.

8. The dental appliance of claim 1, wherein upon removal of the external stimulus, the dental appliance cools below the first glass transition temperature and the first segment hardens, thereby increasing a stiffness of the dental appliance.

9. The dental appliance of claim 1, wherein the external stimulus further comprises any of the following: chemicals, light, magnetic forces, cleaning, and a pH agent.

10. A method for restoring a dental appliance comprising:
    forming the appliance with a plurality of polymeric layers to have a concave trough configured to transition from a first shape to a second shape when a deforming force is applied to the dental appliance, wherein the first shape conforms to a plurality of teeth when placed over the plurality of teeth and applies a first force on the plurality of teeth, the concave trough including a shape memory material; and
    restoring the concave trough from the second shape to an approximate first shape upon an application of an external stimulus, the approximate first shape configured to apply the first force on the plurality of teeth, wherein the shape memory material comprises:
    a first segment being an inner layer, wherein the first segment comprises:
    a first glass transition temperature; and
    a second segment coupled with the first segment, the second segment being an outer layer and enclosing the inner layer, wherein the second segment comprises:
    a second glass transition temperature, wherein the first glass transition temperature is less than the second glass transition temperature,
    wherein upon the application of the external stimulus which comprises heat to cause a temperature to be reached that is higher than or equal to the first glass transition temperature and below the second glass transition temperature, the second segment, being harder than the first segment, controls the first segment via forces to return the concave trough to the approximate first shape, such that as the first segment reaches the first glass transition temperature, the first segment undergoes a state change, molding to a shape of the second segment while the forces of the second segment return the concave trough to the approximate first shape.

11. A method for restoring a dental appliance comprising:

forming a concave trough configured to transition from a first shape to a second shape when a deforming force is applied to the dental appliance, wherein the first shape conforms to a plurality of teeth when placed over the plurality of teeth and applies a first force on the plurality of teeth, the concave trough including a shape memory material; and applying an external stimulus to transition the concave trough to an approximate first shape from the second shape, the approximate first shape configured to apply the first force on the plurality of teeth, wherein the shape memory material comprises:

a first segment being an inner layer, wherein the first segment comprises:
  a first glass transition temperature; and
a second segment coupled with the first segment, the second segment being an outer layer and enclosing the inner layer, wherein the second segment comprises:
  a second glass transition temperature, wherein the first glass transition temperature is less than the second glass transition temperature, wherein upon the application of the external stimulus which comprises heat to cause a temperature to be reached that is higher than or equal to the first glass transition temperature and below the second glass transition temperature, the second segment, being harder than the first segment, controls the first segment via forces to return the concave trough to the approximate first shape, such that as the first segment reaches the first glass transition temperature, the first segment undergoes a state change, molding to a shape of the second segment while the forces of the second segment return the concave trough to the approximate first shape.

12. The method of claim 11, wherein the shape memory material comprises a material selected from the group consisting of shape memory polymers, methacrylate containing polymers, acrylate containing polymers, elastomer polymers, thermoplastic polymers, thermoplastic elastomer polymers, thermoset polymers, thermoplastic polymer blends, cross-linked thermoplastic polymers, cross-linked thermoplastic polymer blends, metal alloys, and shape memory metals.

13. The method of claim 11, wherein the concave trough comprises a plurality of polymeric layers.

14. The method of claim 11, wherein the external stimulus further comprises any of the following: chemicals, light, magnetic forces, cleaning, and a pH agent.

15. The method of claim 11, wherein the second shape is configured to apply a second force on the tooth, the first force being greater than the second force.

16. The method of claim 11, wherein the deforming force comprises a force from the group consisting of inserting the dental appliance, removing the dental appliance, wearing the dental appliance, biting the dental appliance, heating the dental appliance, cooling the dental appliance, and material stress relaxation of the dental appliance.

17. The method of claim 11, further comprising inserting the dental appliance into a cleaning device, wherein the cleaning device is configured to induce one or more external stimuli.

\* \* \* \* \*